(12) United States Patent (10) Patent No.: US 7,277,751 B2
Dupelle et al. (45) Date of Patent: Oct. 2, 2007

(54) ECG/PACING ELECTRODES

(75) Inventors: Michael R. Dupelle, N. Attleboro, MA (US); Sheldon S. White, Brookline, MA (US); Paul Prew, S. Attleboro, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 154 days.

(21) Appl. No.: 10/958,987

(22) Filed: Oct. 5, 2004

(65) Prior Publication Data

US 2006/0074452 A1 Apr. 6, 2006

(51) Int. Cl.
*A61N 1/00* (2006.01)

(52) U.S. Cl. .......................................... 607/4

(58) Field of Classification Search ............ 607/2, 607/4, 142, 152; 600/391
See application file for complete search history.

(56) References Cited

U.S. PATENT DOCUMENTS

| | | | |
|---|---|---|---|
| 4,955,381 A | 9/1990 | Way et al. | |
| 5,080,097 A * | 1/1992 | Eisenberg | 607/2 |
| 5,080,099 A | 1/1992 | Way et al. | |
| 6,019,877 A | 2/2000 | Dupelle et al. | |
| 6,532,379 B2 | 3/2003 | Stratbucker | |
| 2004/0193222 A1 | 9/2004 | Sullivan | |

* cited by examiner

*Primary Examiner*—George Manuel
(74) *Attorney, Agent, or Firm*—Fish & Richardson P.C.

(57) ABSTRACT

A medical electrode assembly comprising a first electrically conductive element configured to be in electrical contact with the patient and to deliver a therapy pulse, a second electrically conductive element configured to be in electrical contact with the patient and to deliver a depolarizing current, and an electrically conductive material providing an electrical connection between the first and second electrically conductive elements and the patient, wherein the first and second electrically conductive elements are configured so that polarization that occurs on the first element as the result of delivery of the therapy pulse may be reduced by subsequent delivery of the depolarizing current, which flows in a circuit that includes the patient and both the first and second conductive elements.

11 Claims, 2 Drawing Sheets

ECG/PACING ELECTRODES

TECHNICAL FIELD

This invention relates to medical electrodes, and more particularly to multi-function electrodes for use in ECG monitoring, external pacing or defibrillation.

BACKGROUND

Medical electrodes typically include the following layers: (a) a pliable plastic foam pad which is used as the mechanical supporting platform for the other electrode components, (b) an electrically conductive element, for example a thin sheet of tin, silver-silver chloride, or other conductive material, and (c) an electrically conductive electrolyte layer, such as a sponge loaded with wet electrolyte or a self-contained hydrogel electrolyte layer. Electrodes may include other ancillary components such as adhesive layers and protective coverings. The layering sequence of the layers described above would normally be (a),(b),(c), with (c) being utilized closest to the patient and in contact with an electrically conductive organ such as the skin. In normal usage for ECG monitoring or delivery of pacing or defibrillation therapy, these multi-function electrodes would be used in pairs with one being placed on the front of the patient's chest near the apex of the heart and the second electrode being placed either on the skin adjacent the patient's sternum or on the patient's back.

Such medical electrodes are commonly used with electrical instruments to monitor a bioelectrical signal of a patient, e.g., an ECG waveform. Medical electrodes are also typically used to deliver a therapeutic electrical stimulus to the patient, for example a cardiac pacing or defibrillation stimulus.

A typical electrode will have a conductive element made out of metal and/or metal salts plus an electrolyte to couple the conductive element with the patient's skin. During both the acquisition of bioelectrical signals from a patient or the delivery of therapeutic pulses to a patient an electrochemical reaction occurs at the interface of the conductive element and the electrolyte. The exact nature of this electrochemical reaction is dependent on the materials used in the conductive element, how they react with the chemicals in the electrolyte, and the magnitude of the electrical pulse. One such electrochemical reaction, commonly known as polarization, is common to all currently used material combinations for conductive elements and electrolytes when exposed to an electrical pulse. Polarization occurs at the interface of the conductive element and the electrolyte, and its magnitude is largely dependent on the magnitude of the electrical pulse to which it is exposed. As a result, it has not previously been practical to use the conductive elements of a multi-function electrode to acquire an ECG signal immediately following the delivery of a pacing or defibrillation pulse, because the polarization potential (or offset voltage) immediately after a pulse can be on the order of 500-1000 millivolts and the ECG signal to be acquired from the patient typically has a magnitude of a few millivolts.

Therefore, separate ECG electrodes, well spaced away from the pacing or defibrillation electrodes, have historically been required in order to "see" the patient's ECG immediately following a pacing or defibrillation pulse. (Way U.S. Pat. Nos. 4,955,381 and 5,080,099 and Stratbucker U.S. Pat. No. 6,532,379).

SUMMARY

In general, the invention features a medical electrode assembly comprising a first electrically conductive element configured to be in electrical contact with the patient and to deliver a therapy pulse, a second electrically conductive element configured to be in electrical contact with the patient and to deliver a depolarizing current, and an electrically conductive material providing an electrical connection between the first and second electrically conductive elements and the patient, wherein the first and second electrically conductive elements are configured so that polarization that occurs on the first element as the result of delivery of the therapy pulse may be reduced by subsequent delivery of the depolarizing current, which flows in a circuit that includes the patient and both the first and second conductive elements.

Preferred implementations may incorporated one or more of the following. There may be a substrate supporting the first and second electrically conductive elements and the electrically conductive material. The electrically conductive material may comprise a conductive gel. The conductive gel may be a solid gel. The solid gel may be a water-based hydrogel. The electrically conductive material may comprise a saline solution. The conductive gel may be a liquid gel. The first and second electrically conductive elements may have different chemical compositions. The first and second electrically conductive element may have the same chemical composition. The second electrically conductive element generally may surround the periphery of the first electrically conductive element.

In another aspect, the invention features a method of treating a patient comprising (a) applying a pair of medical electrodes to the patient, each electrode including a first and a second electrically conductive element in electrical contact with the patient, (b) delivering a therapeutic stimulus to the patient through the first electrically conductive elements of the electrodes, (c) monitoring a cardiac signal from the patient through the first electrically conductive elements of the electrodes, and wherein steps (b) and (c) are repeated sequentially, and wherein the method further comprises (d) delivering a depolarizing current in a circuit including the first and second electrically conductive elements and the patient, to depolarize the first electrically conductive elements generally following step (b) and prior to step (c).

Among the many advantages of the invention (some of which may be achieved only in some of its various aspects and implementations) are the following: The invention may provide a way of obtaining sufficient depolarization of a multi-function electrode in a short enough time period to allow ECG monitoring to take place very soon after a pacing or defibrillation pulse (e.g., before the next pacing pulse). It may make it possible to avoid using separate ECG electrodes and the inconvenience of a separate ECG cable and or machine, especially during resuscitation attempts.

Other features and advantages of the invention will be apparent from the description and drawings, and from the claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
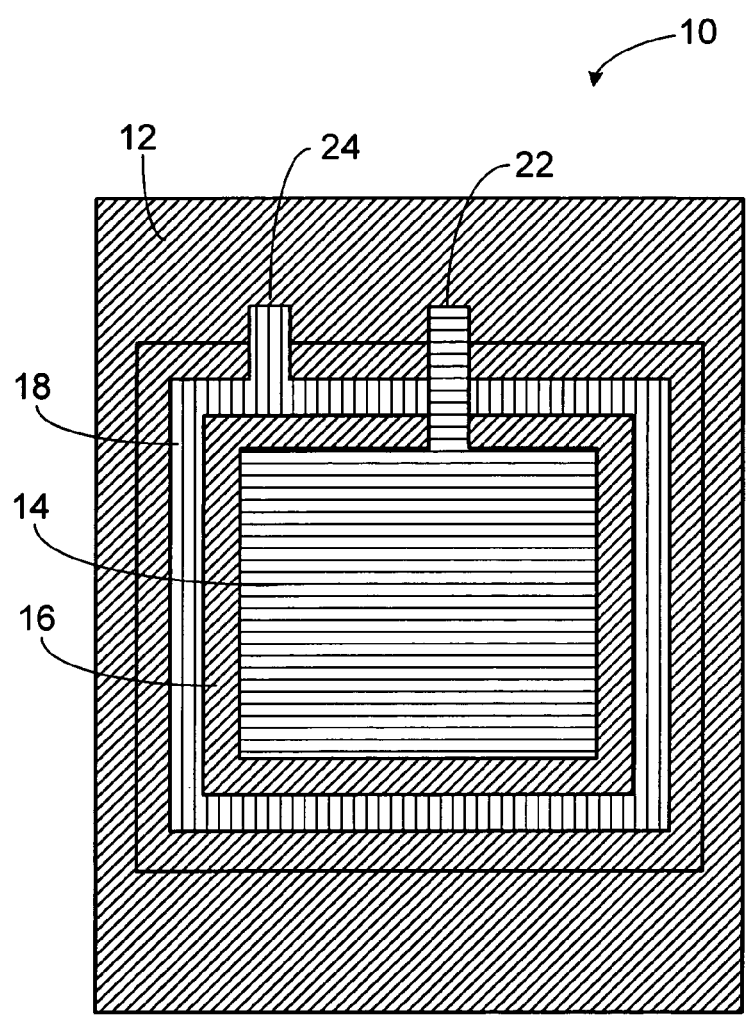
FIG. 1 is a top view of one implementation of the invention.
Figure 2:
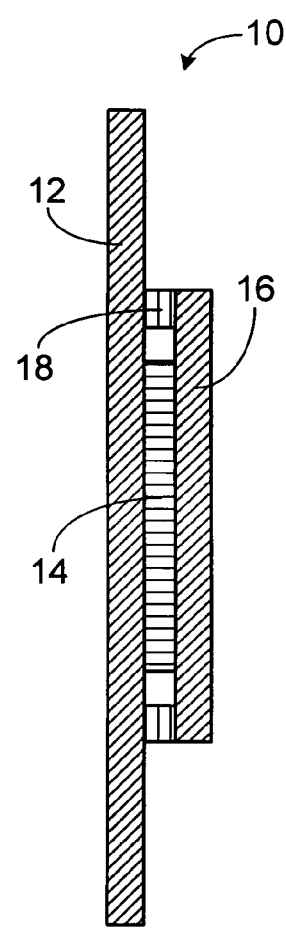
FIG. 2 is a side view of the implementation of FIG. 1.

FIGS. 1-2 shows one possible implementation. Medical electrodes 10 each include a central conductive element 14 surrounded by a depolarizing conductive element 18. The two conductive elements 14, 18 are supported on a foam substrate 12, and in electrical contact with an electrolyte layer 16, which is adhered to the patient's skin. Pacing or other therapy current is delivered to the patient through the central conductive element 14. Depolarizing currents are delivered using depolarizing conductive element 18.

Figure 3:
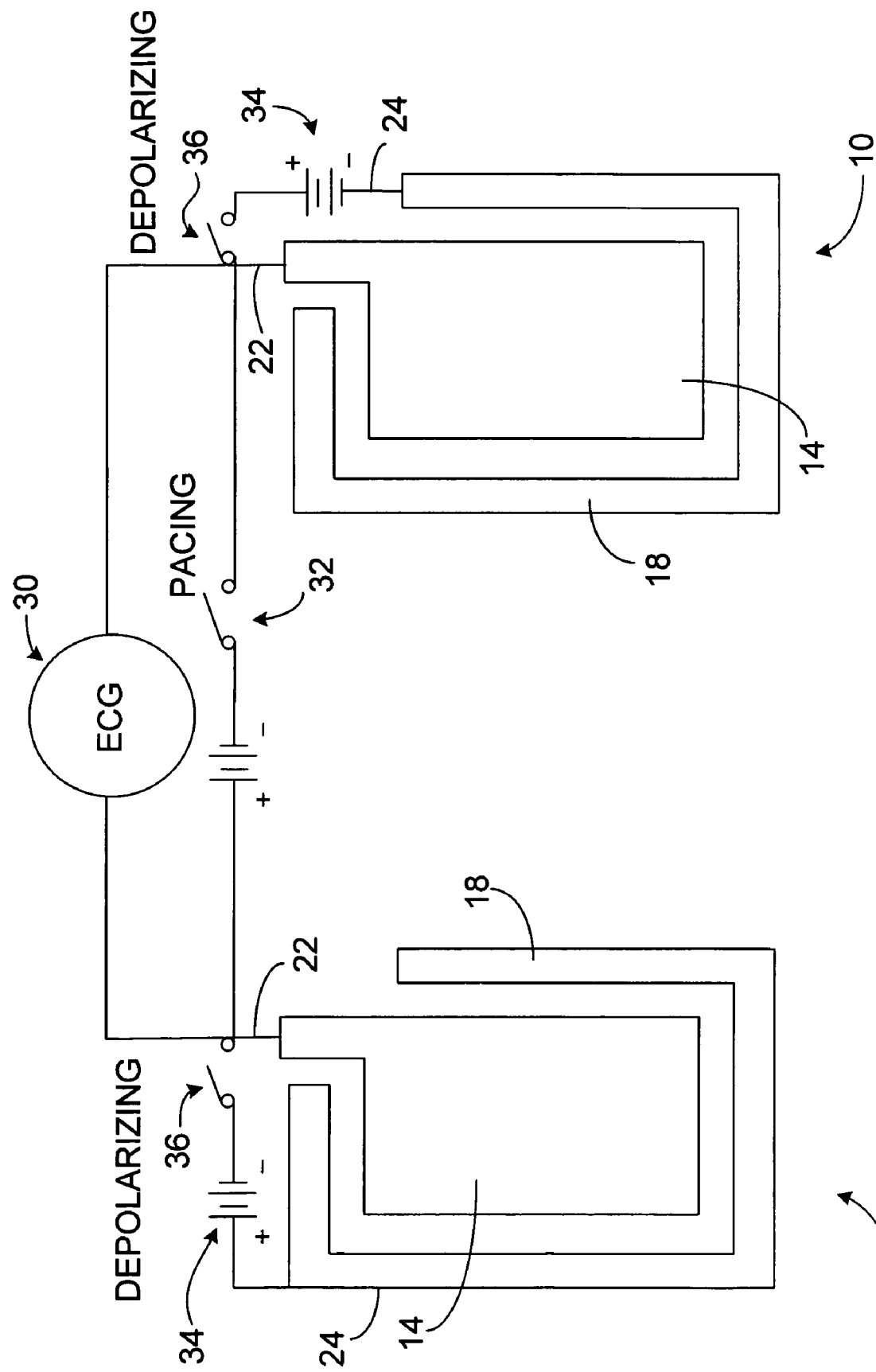
FIG. 3 is an electrical schematic of a pacing implementation using two electrodes of the general type shown in FIGS. 1 and 2.

FIG. 3 is a schematic diagram showing a pair of electrodes 10 connected to ECG monitoring circuitry 30 and pacing circuitry 32. A source 34 of depolarizing current (e.g., a battery) is included in the circuit. Switching mechanisms 36 are included to allow the medical electrodes 10 to be reconfigured immediately preceding and immediately following the pacing pulse. Various types of switching mechanisms may be used, including both solid-state electronic switches and mechanical relays. Wires 22, 24 make electrical connections to the central conductive elements 14 and the depolarizing elements 18, respectively. Wire 24 allows controlled electrical currents to be delivered to the depolarizing element 18 by electrical circuitry that delivers short-term, controlled amounts of energy, sufficient to depolarize the electrically conductive element 14 after it has been polarized by a prior pacing pulse. The depolarizing current flows in a direction that negates (depolarizes) the undesirable polarization effects that take place on the electrically conductive element 14 during pacing, thus allowing the medical electrode 10 to be used sequentially for both monitoring of cardiac signals and delivery of electrical stimuli. Although pacing is shown in FIG. 3, the same depolarization process can be used following a defibrillation pulse.

While a single electrode is shown in FIGS. 1 and 2, a pair of such electrodes would typically be used on a patient, with each of the electrodes typically having the structure shown. The electrodes would normally be adhered to a patient's skin and a cable from each electrode (each cable containing discrete wires 22, 24) would be attached to the ECG and pacing (or defibrillation) circuitry.

Many other implementations of the invention other than those described above are within the invention, which is defined by the following claims. For example, the depolarizing conductive element does not need to surround the main conductive element. The depolarizing element could also serve as a sacrificial element of the type disclosed in U.S. Pat. No. 6,019,877 (incorporated by reference). The electrodes could include an additional conductive element for measuring the general level of polarization of conductive element 14; the additional conductive element may be utilized in an active, closed-loop feedback fashion to maintain a minimal polarization even under circumstances where repetitious long-term delivery of stimuli could otherwise tend to slowly and cumulatively polarize the medical electrode 10 to such an extent that it would become unusable. The electrically conductive elements 14, 18 could have the same or different chemical composition, and they could take a variety of mechanical forms (e.g., sheet metal, printed conductive layers, expanded metal, metal screen).

What is claimed is:

1. A medical electrode assembly comprising:
   a first electrically conductive element connected to a pacing circuitry and configured to be in electrical contact with the patient and to deliver a pacing pulse;
   a second electrically conductive element connected to a depolarizing current source and configured to be in electrical contact with the patient and the first electrically conductive element to deliver a depolarizing current; and
   an electrically conductive material providing an electrical connection between the first and second electrically conductive elements and the patient,
   wherein the first and second electrically conductive elements are configured so that polarization that occurs on the first element as the result of delivery of the pacing pulse may be reduced by subsequent delivery of the depolarizing current, which flows in a circuit that includes the patient and both the first and second conductive elements.

2. The medical electrode assembly of claim 1 further comprising a substrate supporting the first and second electrically conductive elements and the electrically conductive material.

3. The medical electrode assembly of claim 1 wherein the electrically conductive material comprises a conductive gel.

4. The medical electrode assembly of claim 3 wherein the conductive gel is a solid gel.

5. The medical electrode assembly of claim 4 wherein the solid gel is a water-based hydrogel.

6. The medical electrode assembly of claim 3 wherein the conductive gel is a liquid gel.

7. The medical electrode assembly of claim 1 wherein the electrically conductive material comprises a saline solution.

8. The medical electrode assembly of claim 1 wherein the first and second electrically conductive elements have different chemical compositions.

9. The medical electrode assembly of claim 1 wherein the first and second electrically conductive element have the same chemical composition.

10. The medical electrode assembly of claim 1 wherein the second electrically conductive element generally surrounds the periphery of the first electrically conductive element.

11. A method of treating a patient with pacing pulses, comprising
   (a) applying a pair of medical electrodes to the patient, each electrode including a first and a second electrically conductive element in electrical contact with the patient;
   (b) delivering a therapeutic pacing stimulus to the patient through the first electrically conductive elements of the electrodes;
   (c) monitoring a cardiac signal from the patient through the first electrically conductive elements of the electrodes; and
   wherein steps (b) and (c) are repeated sequentially, and wherein the method further comprises
   (d) delivering a depolarizing current in a circuit including the first and second electrically conductive elements and the patient, to depolarize the first electrically conductive elements generally following step (b) and prior to step (c).

* * * * *